United States Patent [19]
Hoos

[11] Patent Number: 6,116,905
[45] Date of Patent: Sep. 12, 2000

[54] METHOD OF TAKING DENTAL IMPRESSIONS

[76] Inventor: Jeffrey C. Hoos, 61 Country Club Dr., Hamden, Conn. 06514-1343

[21] Appl. No.: 09/184,156

[22] Filed: Nov. 2, 1998

[51] Int. Cl.$^7$ ........................................................ A61C 9/00
[52] U.S. Cl. .............................................. 433/214; 264/16
[58] Field of Search ..................................... 433/214, 223, 433/226; 264/16, 17, 18, 19

Primary Examiner—John J. Wilson
Assistant Examiner—Patrick A. Hilsmier
Attorney, Agent, or Firm—Alfred E. Miller

[57] ABSTRACT

A method of taking dental impressions for various types of dental work which is a two step process with only one tray insertion. The impression materials are selected and have durometer measurements which permit a technique without the use of a retraction cord, and the materials are highly thixotropic providing accurate results with a minimum of patient discomfort.

10 Claims, 2 Drawing Sheets

METHOD OF TAKING DENTAL IMPRESSIONS

The present invention relates to a dental impression technique based upon the hydraulic and hydrophobic properties of the selected dental impression materials that result in rapid and faithful reproduction of dental crowns, bridges, inlays, onlays, implants and veneer preparations.

In the past, dental patients experienced discomfort when the dentist takes an impression of the patient's teeth since it is a time consuming technique. The procedure can be further uncomfortable for the patient if the impression materials run or slump, thus activating the patient's gag reflex. Also, in the past, the dentist, when making an impression initially wraps a cord around the tooth to create a space between the gum and tooth after the card is removed, and then applies the impression material.

It is known to use dental impression materials, such as vinyl polysiloxane, with a durometer measurement of 75 in the procedure of taking an impression of a patients teeth in preparation for dental procedures. However, the taking of dental impressions is uncomfortable for the patient and therefore it is desirable to shorten the time period of the impression taking.

SUMMARY OF THE INVENTION

In order to overcome the drawbacks of the prior procedures it is an object of the present invention to provide a dental impression taking procedure in which the time period for completing the procedure is 30 seconds faster than previous methods.

The present invention has been developed to maximize patient comfort and to yield accurate and rapid results by eliminating the use of a retraction cord and while using a different procedure.

An object of the present invention is to provide an impression taking method, which eliminates the use of a retraction cord in the procedure.

It is a further object of the present invention to provide a two step process with only one tray insertion.

It is another feature of the present invention to utilize elastomeric impression materials having different durometer measurement readings to ensure accurate results.

It is a further feature of the present invention to provide a dual arch tray for a double bite impression procedure that is rapid and distortion free.

It is another feature of the present invention to provide a second material over the base material in a dental impression method which is hydraulically moved into the gingival sulcus, and which is hydrophobic.

The above and other objects and features of the invention will be apparent by reference to the following description of my invention and drawings.

DESCRIPTION OF THE PREFERRED EMBODIMENT

In order to practice the present method or procedure the tooth or teeth have to be prepared in which the area affected is thoroughly irrigated with water, and thereafter air-dried. It should be noted that because of the physical properties of the elastomeric impression materials and the sequence of their use no retraction cord for any tooth is necessary. Initially, a double arch impression tray is used which is placed in the patient's mouth to assess size and clearance. If satisfactory, the first impression material, which is preferably vinyl polysiloxane, is dispensed by syringe into the top and bottom of the tray. While extruding the material in the tray the tip of the dispensing syringe is maintained submerged into the impression material to thereby prevent introducing air bubbles into the mix. The first vinyl polysiloxane material selected is thixotropic so that the material holds and spreads in both the top and bottom of the tray. The durometer measurements of the materials are of particular importance. In the present case, the durometer measurement of the first material is 85.

In order to accomplish the present double bite technique, the tray with material in the top and bottom is placed in the patient's mouth and the patient is instructed to close his teeth firmly together and the material is allowed to set for approximately two minutes. Additional material may be placed in the tray prior to setting, if necessary.

After the material sets the patient is instructed to open his or her mouth and the tray is pressed on the teeth opposite the prepared site in the opposing direction. The second step in the process is now performed in which a small amount of wash material, being a second vinyl polysiloxane of a lower durometer measurement reading of 40, is syringed into the impression of the prepared tooth or teeth to laminate to the first material that has been set.

Figure 1:
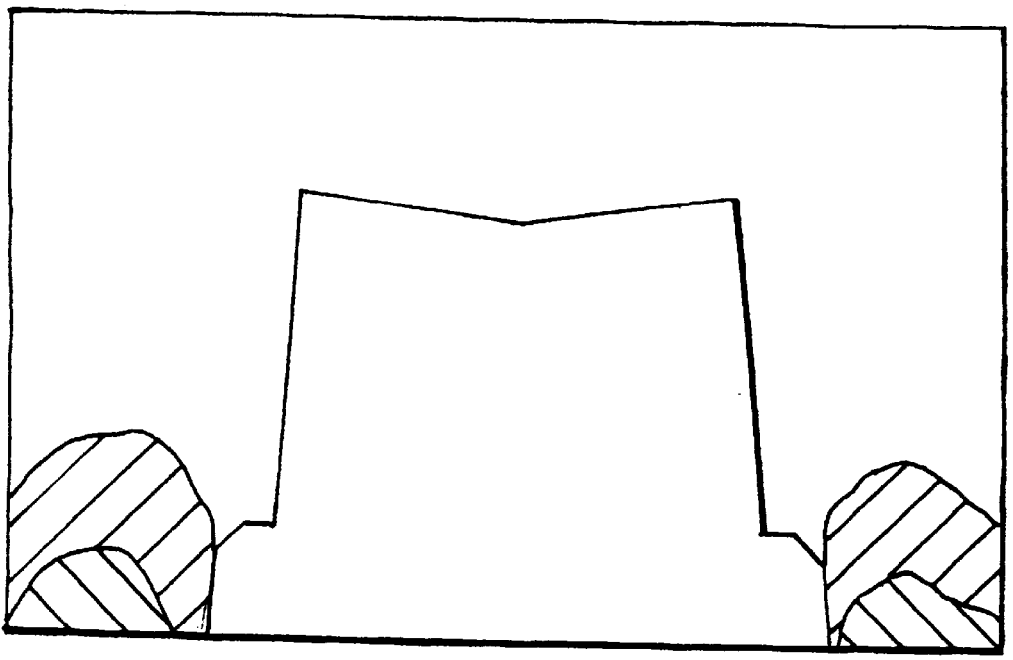
FIG. 1 is a diagrammatic view of the commencement of the first step of the two step impression taking procedure in accordance with the teachings of my invention.
Figure 2:
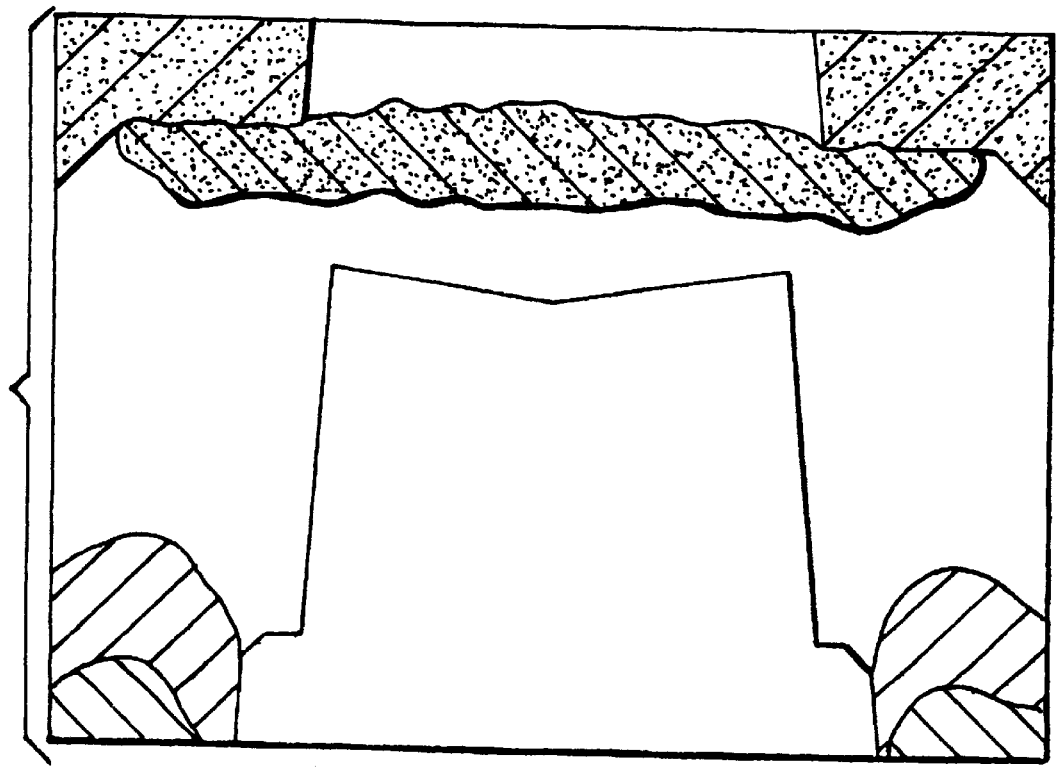
FIG. 2 is a diagrammatic view of the second step of the impression taking procedure of FIG. 1.
Figure 3:
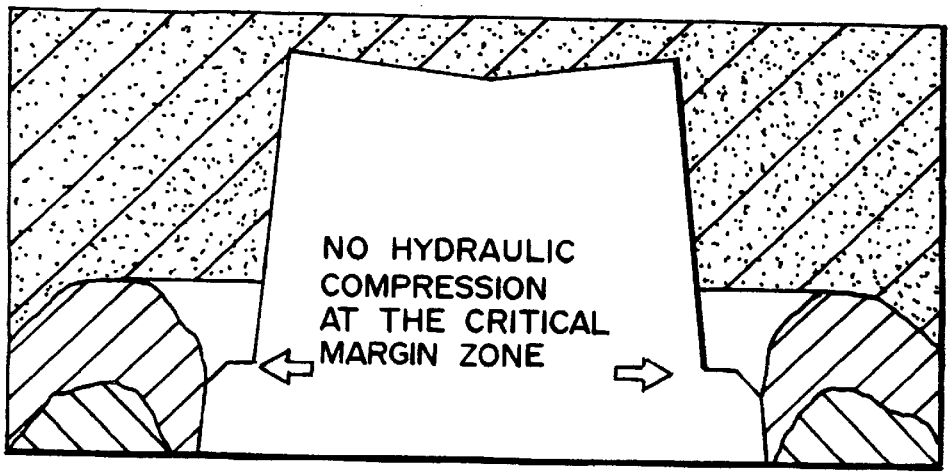
FIGS. 3, 4 and 5 are diagrammatic views of the invention showing the results of the two step process for dental impression taking.
Figure 4:
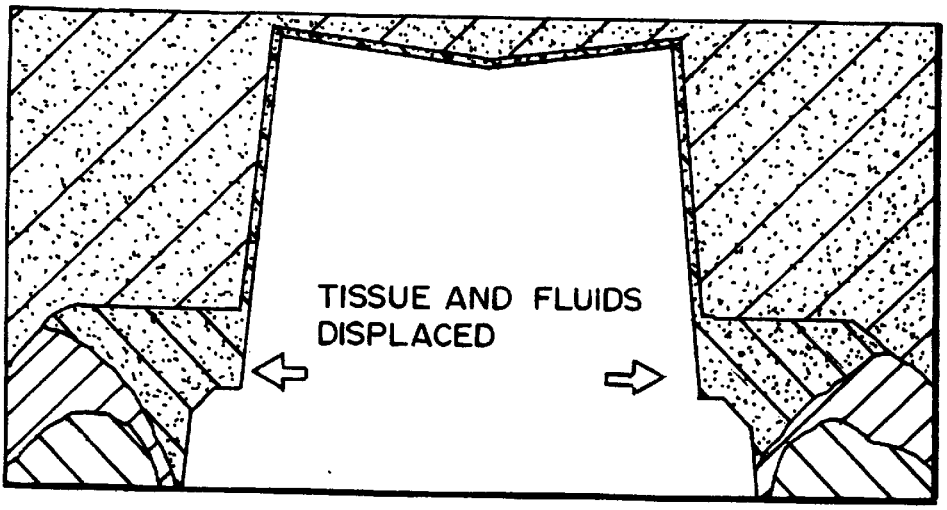
Figure 5:
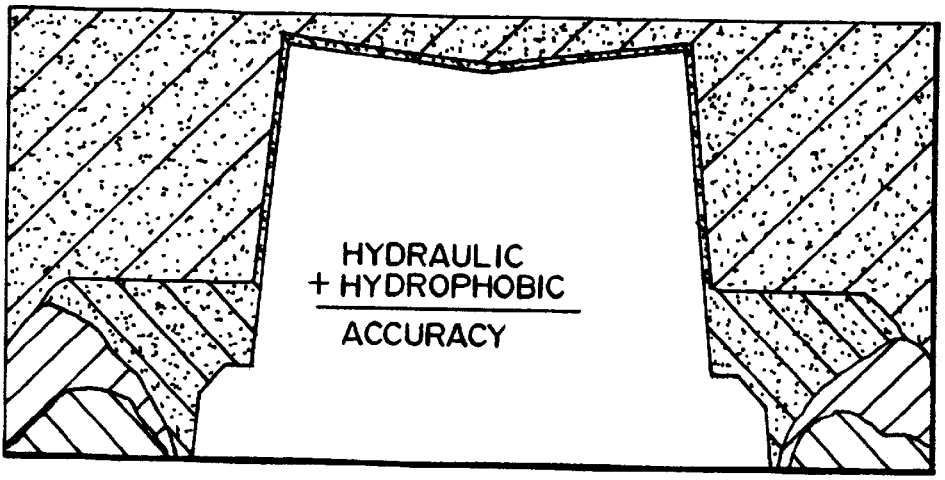

The patient is then instructed to close his or her mouth firmly until the second material is set. Thereafter, the patient opens his or her mouth and the tray is removed. The first or base material exhibits a hard, plastic like set that resists hydraulic pressure thereby minimizing distortions. This result occurs because of the durometer measurement of 85. The second wash material of a durometer measurement of 40 is in a flexible state and is hydraulically forced into place, as seen in FIGS. 3–5. The second wash material is hydraulically moved into the gingival sulcus of the patient thereby displacing the gingival tissue and oral fluids. It, therefore, does not absorb moisture because it is hydrophobic and sets without distortion.

When the second material sets the tray is removed from the mouth. The impression procedure is faster than previous procedures by about 30 seconds thus minimizing the discomfort and gagging experience to the patient.

While the invention has been disclosed and described with reference to a single method embodiment it will be apparent that changes and modifications may be made in the method therein and it is intended in the following claims to cover each such variation and modification as falls within the true spirit and scope of the present invention.

What I claim is:

1. A method of dental impression taking for a patient without the use of a retraction cord and following preparation of an oral site comprising:
   a) irrigating an oral cavity with a liquid
   b) air drying the oral site
   c) inserting a double arch impression tray having a top and bottom in the area of said oral site
   d) dispensing a first impression material of durometer measurement of 85 having a high degree of rigidity in both the top and bottom of said tray,
   e) closing the patient's mouth on said tray in a centric position;

f) opening the patient's mouth and pressing said tray on the opposite side of the oral site, g) dispensing a second impression material in the top and bottom of said tray of lower durometer measurement than said first impression measurement, h) said second material having hydrophobic properties being moved hydraulically into the gingival sulcus of said patient when said patient closes his mouth and the material sets, and i) said patient opens his mouth and the tray removed whereby the resulting dental impression has great accuracy in a shorter period of time.

2. A dental impression technique without the use of a retention cord and utilizing materials having hydraulic and hydrophobic properties resulting in the rapid reproduction of prepared oral sites comprising the steps of:

a) preparing at least one tooth for taking of a dental impression having a top and bottom b) inserting a double arch impression tray having a top and bottom in the area of tooth preparation the at least one prepared tooth c) dispensing a first thixotropic impression material of 85 durometer measurement in both the top and bottom of said tray, d) closing the patient's mouth and pressing said tray on the dental arch opposite to said preparation, e) opening the patient's mouth and pressing said tray on the dental arch opposite to said at least one prepared tooth f) dispensing a second thixotropic impression material of a durometer measurement of 40 in the top and bottom of said tray, g) said second impression material having hydrophobic properties and being moved hydraulically into the gingival sulcus of said patient when said patient closes his mouth and material sets, and said patient opens his mouth and the tray removed whereby the resulting dental impression has great accuracy in a shorter period of time.

3. The method of claim 2 wherein said impression materials are vinyl polysiloxane.

4. The method of claim 2 wherein said second impression material is flexible.

5. The method of claim 2 wherein said technique is utilized for making dental impressions for creating dental bridges.

6. The method of claim 2 wherein said technique is utilized for making dental impression for dental crowns.

7. The method of claim 2 wherein said technique is utilized for making dental impressions for dental implants.

8. The method of claim 2 wherein said technique is utilized for making dental impressions for dental inlays.

9. The method of claim 2 wherein said technique is utilized for making dental impressions for dental onlays.

10. The method of claim 2 wherein said technique is utilized for making dental impressions for dental veneers.

* * * * *